(12) United States Patent
Rezai et al.

(10) Patent No.: US 9,108,057 B2
(45) Date of Patent: Aug. 18, 2015

(54) METHODS OF TREATING MEDICAL CONDITIONS BY TRANSVASCULAR NEUROMODULATION OF THE AUTONOMIC NERVOUS SYSTEM

(75) Inventors: Ali Rezai, Bratenahl, OH (US); Mehdi Ansarinia, Las Vegas, NV (US)

(73) Assignee: The Cleveland Clinic Foundation, Cleveland, OH (US)

( * ) Notice: Subject to any disclaimer, the term of this patent is extended or adjusted under 35 U.S.C. 154(b) by 330 days.

(21) Appl. No.: 12/902,857

(22) Filed: Oct. 12, 2010

(65) Prior Publication Data

US 2011/0029037 A1 Feb. 3, 2011

Related U.S. Application Data

(60) Division of application No. 11/222,766, filed on Sep. 12, 2005, now abandoned, which is a continuation-in-part of application No. 11/121,006, filed on May 4, 2005, now Pat. No. 7,877,146.

(60) Provisional application No. 60/567,441, filed on May 4, 2004, provisional application No. 60/608,420, filed on Sep. 10, 2004, provisional application No. 60/608,513, filed on Sep. 10, 2004.

(51) Int. Cl.
*A61N 1/36* (2006.01)
*A61N 1/05* (2006.01)
*A61B 5/00* (2006.01)
*A61M 5/00* (2006.01)

(52) U.S. Cl.
CPC ............ *A61N 1/36082* (2013.01); *A61B 5/411* (2013.01); *A61B 5/415* (2013.01); *A61B 5/418* (2013.01); *A61M 5/00* (2013.01); *A61N 1/3611* (2013.01); *A61N 1/36021* (2013.01); *A61N 1/36071* (2013.01); *A61N 1/36085* (2013.01); *A61N 1/36089* (2013.01); *A61N 1/0551* (2013.01)

(58) Field of Classification Search
CPC ... A61N 1/05; A61N 1/0551; A61N 1/36082; A61N 1/36085; A61M 5/00; A61B 5/4029; A61B 5/4058; A61B 5/6877
USPC .......................... 857/381; 607/2, 40; 600/381
See application file for complete search history.

(56) References Cited

U.S. PATENT DOCUMENTS

| | | | |
|---|---|---|---|
| 5,540,730 A | 7/1996 | Terry, Jr. et al. | |
| 5,861,014 A | 1/1999 | Familoni | |
| 6,026,326 A | 2/2000 | Bardy | |
| 6,058,331 A | 5/2000 | King | |
| 6,356,786 B1 * | 3/2002 | Rezai et al. | 607/45 |
| 6,356,787 B1 * | 3/2002 | Rezai et al. | 607/45 |
| 6,438,423 B1 * | 8/2002 | Rezai et al. | 607/46 |
| RE38,654 E | 11/2004 | Hill et al. | |
| 6,885,888 B2 * | 4/2005 | Rezai | 607/9 |
| 7,363,076 B2 | 4/2008 | Yun et al. | |
| 7,449,018 B2 * | 11/2008 | Kramer | 606/21 |
| 7,584,004 B2 * | 9/2009 | Caparso et al. | 607/118 |
| 7,599,736 B2 | 10/2009 | DiLorenzo | |
| 7,689,276 B2 | 3/2010 | Dobak | |
| 7,877,146 B2 * | 1/2011 | Rezai et al. | 607/42 |
| 2003/0181958 A1 | 9/2003 | Dobak, III | |
| 2004/0172084 A1 | 9/2004 | Knudson et al. | |
| 2004/0236381 A1 | 11/2004 | Dinsmoor et al. | |
| 2006/0085046 A1 * | 4/2006 | Rezai et al. | 607/40 |
| 2010/0145408 A1 | 6/2010 | Dobak, III | |

* cited by examiner

*Primary Examiner* — Christopher A Flory
(74) *Attorney, Agent, or Firm* — Tarolli, Sundheim, Covell & Tummino L.L.P.

(57) ABSTRACT

The present invention is directed to a method for treating a gastrointestinal condition by transvascular neuromodulation of a target site of the autonomic nervous system and preferably a target site in communication with a sympathetic nerve chain. A method for treating a gastrointestinal condition via transvascular neuromodulation incorporating a closed-loop feedback system is also provided.

11 Claims, No Drawings

METHODS OF TREATING MEDICAL CONDITIONS BY TRANSVASCULAR NEUROMODULATION OF THE AUTONOMIC NERVOUS SYSTEM

CROSS-REFERENCE TO RELATED APPLICATIONS

The present application is a divisional application of U.S. Ser. No. 11/222,766, filed on Sep. 12, 2005, now abandoned which is a continuation-in-part of U.S. application Ser. No. 11/121,006, filed on May 4, 2005 now U.S. Pat. No. 7,877, 146, which claims priority to U.S. Provisional Application Nos. 60/567,441, filed on May 4, 2004; 60/608,420, filed on Sep. 10, 2004; and 60/608,513, filed on Sep. 10, 2004.

FIELD OF THE INVENTION

The present invention relates to methods of treating medical conditions by transvascular electrical and/or chemical neuromodulation of target sites in the autonomic nervous system.

BACKGROUND OF THE INVENTION

Neuromodulation involves an array of therapeutic approaches applied to the brain, cranial nerves, spinal cord and all associated nerves and neural structures in the human body to treat various human disorders. Neuromodulation can involve lesioning, electrical stimulation, chemical stimulation/modulation as well as gene therapy and administration of stem cells. Electrical stimulation of neural tissue is becoming an increasingly preferred form of therapy for certain neurological conditions and disorders where existing therapies generate intolerable side effects, require repeated administration of treatment, or are simply ineffective in a subset of patients. Electrical stimulation provides distinct advantages over surgical lesioning techniques since electrical stimulation is a reversible and adjustable procedure that provides continuous benefits as the patient's disease progresses and the patient's symptoms evolve.

Currently, electrical stimulation of peripheral nerves and the spinal cord is approved for treatment of neuropathic pain. With respect to deep brain targets, electrical stimulation of the subthalamic nucleus and the globus pallidus interna is approved for treatment of Parkinson's disease and electrical stimulation of the ventral intermediate nucleus is approved for treatment of essential tremor.

There remains a need for further forms of neuromodulation to treat these and other disorders.

SUMMARY OF THE INVENTION

In an embodiment, the present invention provides a method for treating a medical condition comprising inserting a therapy delivery device in a vessel of a body and advancing the therapy delivery device to a point in the vessel adjacent a target site of the autonomic nervous system. The method further comprises activating the therapy delivery device to deliver a therapy signal to the target site to treat the medical condition.

The medical conditions that can be treated by methods of the present invention include skeletal, immunological, vascular/hematological, muscular/connective, neurological, visual, auditory/vestibular, dermatological, endocrinological, olfactory, cardiovascular, reproductive, urinary, psychological, gastrointestinal, respiratory/pulmonary, inflammatory, infectious (bacterial, viral, fungal, parasitic), traumatic, iatrogenic, drug induced and neoplastic medical and surgical conditions.

The present invention also provides methods of stabilizing and optimizing bodily functions perioperatively and/or postoperatively by transvascularly neuromodulating a target site of the autonomic nervous system.

DETAILED DESCRIPTION OF THE INVENTION

The present invention provides methods for treating medical conditions by transvascular neuromodulation of a target site of an autonomic nervous system and preferably transvascular neuromodulation of a target site in communication with a sympathetic nerve chain and all of the associated structures and nerves in communication with the sympathetic nerve chain.

The autonomic nervous system is divided into two divisions, the sympathetic nervous system and the parasympathetic nervous system. The sympathetic nervous system includes the sympathetic nerve chains and its associated direct and indirect input and output nerve branches, nerve clusters, nerve aggregates, and nerve plexuses located, for example, in the skull including input from the brain, spinal cord, base of the skull, neck, thoracic, abdominal, and pelvic cavities, and their associated arterial and venous structures. The sympathetic nerve chain (also known as the sympathetic nerve trunk) is a long ganglionated nerve strand along each side of the vertebral column that extends from the base of the skull to the coccyx. Each sympathetic nerve chain is connected to each spinal nerve by gray rami and receives fibers from the spinal cord through white rami connecting with the thoracic and upper lumbar spinal nerves. A sympathetic nerve chain has paravertebral ganglia that are connected by a paravertebral sympathetic chain. Target sites in communication with the sympathetic nerve chain, according to the present invention, are target sites in the nervous system having fibers that project to and/or from the sympathetic nerve chain. Examples of such target sites include the superior cervical, middle cervical, vertebral, inferior cervical and cervicothoracic ganglia, spinal cord segments T1 to L3; sympathetic ganglia (including paravertebral ganglia and prevertebral ganglia), paravertebral sympathetic chain, thoracic and lumbar sympathetic ganglia, nerve plexuses in communication with sympathetic ganglia, dorsal roots, ventral roots, dorsal root ganglia, dorsal rami, ventral rami, white rami communicans, gray rami communicans, and recurrent meningeal branches, all emerging from spinal cord segments T1 to L3; T1 to L3 spinal nerves; and any combination of the above from one or both of the sympathetic nerve chains. Thoracic and lumbar ganglia and prevertebral ganglia and their associated sympathetic structures include the cardiac, celiac, mesenteric (superior and inferior), renal, hypogastric, and intermesenteric (abdominal aortic) ganglia as well as ganglia associated with glands such as hepatic or adrenal glands. Nerve plexuses include prevertebral plexuses such as the superior and inferior hypogastric (pelvic) plexus. Target sites also include the thoracic, lumbar, and sacral splanchnic nerves.

The parasympathetic nervous system includes preganglionic outflow of the arising from the cell bodies of the motor nuclei of the cranial nerves III, VII, IX and X in the brain stem and from the second, third and fourth sacral segments of the spinal cord. Preganglionic fibres run almost to the organ which is innervated, and synapse in ganglia close to or within that organ, giving rise to postganglionic fibers, which then innervate the relevant tissue. Preganglionic axons emerging from the brain stem project to parasympathetic ganglia that are located in the head (ciliary, sphenopalatine, and otic ganglia) or near the heart (cardiac ganglia), embedded in the end organ itself (such as the trachea, bronchi, and gastrointestinal tract), or situated a short distance from the urinary bladder (pelvic ganglion).

The methods of the present invention comprise treating medical conditions by inserting a therapy delivery device, such as an electrode or drug port, into a vessel of the body and advancing the therapy delivery device in the vessel to a point adjacent a target site of the autonomic nervous system. The methods further comprise activating the therapy delivery device to deliver a therapy signal to the target site to treat the medical conditions. In embodiments where the therapy delivery device is an electrode, the therapy signal is an electrical signal and in embodiments where the therapy delivery device is a drug port, the therapy signal is a chemical signal. The therapy delivery device, according to the methods of the present invention, is inserted into any vessel of the body to access the autonomic target site, such as an artery or vein. Non-limiting examples of arteries into which a therapy delivery device can be positioned include the aorta, including the ascending, descending, thoracic, abdominal and arch segments; carotid arteries; femoral arteries; brachial arteries; radial arteries; popliteal arteries; ulnar arteries; dorsalis pedias arteries; intercostals arteries; vertebral arteries; subclavian arteries; iliac arteries; renal arteries and tributaries thereof. Non-limiting examples of types of veins into which a therapy delivery device can be positioned include jugular veins (external and internal), ante-brachial veins, subclavian veins, axillary veins; iliac veins; sinuses; saphenous veins; intercostals veins; radial veins; brachial veins, femoral veins; renal veins, superior vena cava, inferior vena cava, and tributaries thereof. Vessels can be accessed endoscopically, percutaneously, or laproscopically and the entry sites of the therapy delivery devices can be vessels that are the same or different from the vessels in which the therapy delivery devices are ultimately positioned. Non-limiting examples of entry vessels into which a therapy delivery device according to the present invention is initially inserted include the subclavian arteries and veins; femoral arteries and veins; radial arteries and veins; external and internal jugular veins; brachial veins and arteries; carotid arteries; and aorta. Any of the methods of the present invention can be guided by imaging means such as MRI/CT/X-ray/fluoroscopy/ultrasonography, optical imaging.

The methods of the present invention for treating medical conditions encompass neuromodulation of any combination of one or more target sites of the autonomic nervous system, including any combination of one or more target sites in communication with the sympathetic nerve chain. The methods of the present invention also encompass ipsilateral, contralateral, and bilateral neuromodulation.

As used herein, the term "treating" a medical condition encompasses therapeutically regulating, preventing, improving, alleviating the symptoms of, reducing the effects of and/or diagnosing the medical condition. As used herein, the term "medical condition" encompasses any condition, disease, disorder, function, abnormality, or deficit influenced by the autonomic nervous system. Further, the methods of the present invention can be used to treat more than one medical condition concurrently. Non-limiting examples of medical conditions that can be treated according to the present invention include genetic, skeletal, renal, dental, immunological, vascular or hematological, muscular or connective tissue, neurological, ocular, auditory or vestibular, dermatological, endocrinological, olfactory, cardiovascular, reproductive, urinary, psychological, gastrointestinal, respiratory/pulmonary, neoplastic, or inflammatory medical conditions. Further, the medical condition can be the result of any etiology including vascular, ischemic, thrombotic, embolic, infectious (including bacterial, viral, parasitic, fungal, abscessal), neoplastic, drug-induced, metabolic, immunological, collagenic, traumatic, surgical/iatrogenic, idiopathic, endocrinological, allergic, degenerative, congenital, or abnormal malformational causes.

The present invention also encompasses enhancing the therapeutic effects of other therapies, such as methods working in conjunction with a pharmaceutical agent or other therapies to augment, enhance, improve, or facilitate other therapies (adjunctive therapies) as well as reducing/minimize and counteract side effects, complications and adverse reactions for any therapies involved in treating the above-mentioned medical conditions. For example, the methods of the present invention may be used for a cancer patient undergoing chemotherapy utilizing stimulation to minimize the adverse effects of chemotherapy. Alternatively, the methods can be used to enhance chemotherapy, such as to facilitate white blood cell and other immune activity to boost the immune system of people who are to undergo or are undergoing chemotherapy. In addition, the methods of the present invention can be used to modify gene expression within or outside of the nervous system to lead to various expression within cells such as, for example, modulation of surface receptors, secretion of proteins, growth factors, messengers, and cell cycles.

With respect to treating genetic medical conditions, such medical conditions can affect single organs, organ systems, or multiple organs in multiple organ systems.

With respect to treating skeletal medical conditions, such medical conditions can involve any medical conditions related to the components of the skeletal system such as, for example, bones, joints, or the synovium. Non-limiting examples of such skeletal medical conditions include fractures, osteoporosis, osteopenia, and arthritis. Non-limiting examples of vessels into which therapy delivery devices, according to the present invention, are positioned to access autonomic target sites innervating components of the skeletal system are the aorta; inferior vena cava; superior vena cava; inferior and superior thyroid arteries and veins; the carotid arteries and branches, jugular veins and branches; and renal arteries.

With respect to treating immunological, inflammatory, and allergic medical conditions, such medical conditions can involve any medical conditions related to the components of the immune system such as, for example, the spleen or thymus. Non-limiting examples of immunological medical conditions include immuno-suppressed states such as post transplant or chemotherapy, immuno-compromised states such as cancer and AIDS, auto-immune disorders such as lupus; multiple sclerosis; gullian barre; and allergies. Non-limiting examples of vessels into which therapy delivery devices, according to the present invention, are positioned to access autonomic target sites innervating components of the immune system are throughout the venous and arterial system including subclavian arteries and veins; brachial arteries and veins; radial arteries; internal and external jugular veins; veins in the dorsum of the hand; celiac trunk; arteries and veins near lymph nodes and the thymus gland.

With respect to treating vascular or hematological medical conditions, such medical conditions can involve any medical conditions related to the components of the vascular system such as, for example, the arteries; arterioles; veins; venules; capillaries; lymph nodes; blood including plasma, white blood cells, red blood cells, and platelets. Non-limiting examples of vascular/hematological medical conditions include anemia, atherosclerosis, stenosis of the vasculature, hemorrhage, thrombosis, blood loss, stroke, and vasospasms.

With respect to treating muscular/connective tissue medical conditions, such medical conditions can involve any medical conditions related to the components of the muscular/connective tissue system such as, for example, smooth or striated muscles, tendons, ligaments, cartilage, fascia, and fibrous tissue. Non-limiting examples of muscular medical conditions include muscular dystrophy and muscle atrophy. Non-limiting examples of connective tissue medical conditions include scleroderma, rheumatoid arthritis and lupus. Non-limiting examples of vessels into which therapy delivery devices, according to the present invention, are positioned to access autonomic target sites innervating components of the muscular/connective system are arteries and veins projecting to and emanating from striated and/or smooth muscles.

With respect to treating neurological medical conditions, such medical conditions can involve any medical conditions related to the components of the nervous system such as, for example, the brain, spinal cord, and peripheral nerves. Non-limiting examples of neurological conditions include Alzheimer's disease, epilepsy, and ALS. Non-limiting examples of vessels into which therapy delivery devices, according to the present invention, are positioned to access autonomic target sites innervating components of the nervous system are carotid arteries and branches; jugular veins and branches; vertebral arteries and branches; and brachial arteries and branches.

With respect to treating ocular medical conditions, such medical conditions can involve any medical conditions related to the components of the visual system such as, for example, the eye including the lens, iris, lids, cornea, and retina. Non-limiting examples of ocular medical conditions include retinopathies; retinal detachment; macular degeneration; cataracts; glaucoma; and blindness. Non-limiting examples of vessels into which therapy delivery devices, according to the present invention, are positioned to access autonomic target sites innervating components of the visual system are central retinal arteries and veins; ophthalmic veins and arteries; supraorbital arteries and veins; carotid arteries; vorticose veins; arterial circle of iris; and ciliary arteries.

With respect to treating auditory and vestibular medical conditions, such medical conditions can involve any medical conditions related to the components of the auditory and vestibular system such as, for example, the ear including the external ear, the middle ear, the inner ear, cochlea, ossicles, tympanic membrane, and semicircular canals. Non-limiting examples of auditory and vestibular medical conditions include vertigo, hearing loss, dizziness, Menier's disease, and tinnitus. Non-limiting examples of vessels into which therapy delivery devices, according to the present invention, are inserted to access autonomic target sites innervating components of the auditory and vestibular system are carotid arteries; internal auditory arteries; jugular veins; and vertebral arteries and veins.

With respect to treating dermatological medical conditions, such medical conditions can involve any medical conditions related to the components of the skin and integumentary system such as, for example, the hair, skin, nails, and sweat glands. Non-limiting examples of dermatological medical conditions include acne, rosacea, eczema, psoriasis, and hair loss. Non-limiting examples of vessels into which therapy delivery devices, according to the present invention, are positioned to access autonomic target sites innervating components of the skin and integumentary system are the aorta; carotid arteries; subclavian arteries; jugular veins; brachial arteries and veins; and femoral arteries and veins.

With respect to treating endocrinological medical conditions, such medical conditions can involve any medical conditions related to the components of the endocrine system such as, for example, the pancreas, thyroid, adrenal glands, liver, pituitary, and hypothalamus. Non-limiting examples of endocrinological conditions include hypoglycemia, diabetes, obesity, hyperthyroidism, hypothyroidism, chronic fatigue syndrome, and Raynaud's syndrome. Non-limiting examples of vessels into which therapy delivery devices, according to the present invention, are positioned to access autonomic target sites innervating components of the endocrine system are the inferior and superior thyroid arteries and veins; carotid arteries and jugular veins, hypophyseal arteries and veins; celiac trunks; aorta; vena cavas; iliac arteries and veins; mesenteric arteries and veins; and renal arteries and veins.

With respect to treating olfactory medical conditions, such medical conditions can involve any medical conditions related to the components of the olfactory system such as, for example, the nose, sensory nerves for smell, and sinuses. Non-limiting examples of olfactory conditions include loss of sense of smell, rhinitis, rhinorrhea, and sinusitis. Non-limiting examples of vessels into which therapy delivery devices, according to the present invention, are positioned to access autonomic target sites innervating components of the olfactory system are carotid artery and branches; jugular vein and branches; septal arteries; maxillary arteries and veins; and naso-celiary arteries and veins.

With respect to treating cardiovascular medical conditions, such medical conditions can involve any medical conditions related to the components of the cardiovascular system such as, for example, the heart and aorta. Non-limiting examples of cardiovascular conditions include post-infarction rehabilitation, shock (hypovolemic, septic, neurogenic), valvular disease, heart failure, angina, microvascular ischemia, myocardial contractility disorder, cardiomyopathy, hypertension including pulmonary hypertension and systemic hypertension, orthopnea, dyspenea, orthostatic hypotension, dysautonomia, syncope, vasovagal reflex, carotid sinus hypersensitivity, pericardial effusion, heart failure, and cardiac structural abnormalities such as septal defects and wall aneurysms. Non-limiting examples of vessels into which therapy delivery devices, according to the present invention, are positioned to access autonomic target sites innervating components of the cardiovascular system are the carotid arteries; aorta; superior vena cava; inferior vena cava; pulmonary veins and arteries; carotid arteries; and subclavian arteries and veins. In a preferred embodiment, a therapy delivery device is used in conjunction with a pulmonary artery catheter, such as a Swan-Ganz type pulmonary artery catheter to delivery transvascular neuromodulation via the pulmonary artery to an autonomic target site to treat a cardiovascular condition according to the present invention. Specifically, in this preferred embodiment, a therapy delivery device is housed within one of the multiple vessels of a pulmonary artery catheter.

With respect to treating reproductive medical conditions, such medical conditions may involve any medical conditions related to components of the reproductive system such as, for example, the ovary, fallopian tube, uterus, vagina, penis, testicle, prostate, and cervix. Non-limiting examples of reproductive medical conditions include contraception, abortion, menorrhagia, complications of pregnancy, preclampsia, endometriosis, impotence and infertility. Non-limiting examples of vessels into which therapy delivery devices, according to the present invention, are positioned to access autonomic target sites innervating components of the reproductive system are the aorta; iliac arteries and veins; vena cava; testicular arteries and veins; and ovarian arteries and veins.

With respect to treating urinary medical conditions, such medical conditions may involve any medical conditions related to the components of the urinary system such as, for example, the kidney, bladder, ureter, and urethra. Non-limiting examples of genitourinary medical conditions include renal failure, nephrolithiasis, renal insufficiency, spastic bladder, flaccid bladder, and cystitis. Non-limiting examples of vessels into which therapy delivery devices, according to the present invention, are positioned to access autonomic target sites innervating components of the urinary system are the aorta; iliac arteries and veins; vena cava; and renal arteries and veins.

With respect to treating psychological medical conditions, non-limiting examples of such medical conditions include Tourette's Syndrome, mental retardation, anxiety, depression, bipolar disorder, and addictions. The addiction may be to substances or behavior.

With respect to treating gastrointestinal medical conditions, such medical conditions can involve any medical conditions related to the components of the gastrointestinal system such as, for example, the mouth, esophagus, stomach, small intestine, large intestine, rectum, liver, gall bladder, bile ducts, anus, and pancreas. Non-limiting examples of gastrointestinal medical conditions include gastroesophageal reflux disease, gastric/duodenal ulcer, pancreatic insufficiency, chololithiasis, inflammatory bowel disease (Crohn's and ulcerative colitis), diabetes, and visceral pain. Non-limiting examples of vessels into which therapy delivery devices, according to the present invention, are positioned to access autonomic target sites innervating components of the digestive system are the aorta and branches; vena cava and branches; iliac arteries and veins; celiac trunk; and mesenteric arteries and veins.

With respect to treating respiratory/pulmonary medical conditions, such medical conditions can involve any medical conditions related to the components of the respiratory system such as, for example, the trachea, bronchus, bronchioles, alveoli, lungs, and capillaries. Non-limiting examples of respiratory medical conditions include reactive airway disease, asthma, patients requiring ventilatory assistance, adult respiratory distress syndrome (ARDS), emphysema, and COPD (chronic obstructive pulmonary disease). Non-limiting examples of vessels into which therapy delivery devices, according to the present invention, are positioned to access autonomic target sites innervating components of the respiratory system are the carotid arteries; jugular veins; brachiocephalic veins; and pulmonary arteries and veins.

With respect to treating neoplastic processes such processes can be primary and/or metastatic and can involve the thryoid, the liver, the pancreas (including vipoma and insulinoma), leukemia, lymphoma and other non-solid tumors. Neoplastic processes can also affect any of the organs including the brain; stomach; lung; colon; esophagus; nasopharynx; rectum; bone; skin including basal cells, squamous cells, and melanoma; bladder; kidney; prostate; breast; ovaries, and uterus.

With respect to treating inflammatory disorders, such inflammatory disorders include, for example, inflammatory bowel disorders such as irritable bowel syndrome and Crohn's disease; and auto-immune disorders.

The present invention also provides methods of treating pain syndromes. Such pain may result from one or more medical conditions including fibromylagia, low back pain, neck pain, cancer pain, arthritic pain, and headaches including migraine headaches.

In embodiments where the therapy delivery device is an electrode and the therapy signal is an electrical signal, once the electrode is placed in a vessel adjacent an autonomic nervous system site, a pulse generator connected to the electrode is activated thereby applying to the autonomic nervous system target site an oscillating electrical signal having specified pulsing parameters. The oscillating electrical signal may be applied continuously or intermittently and the pulsing parameters, such as the pulse width, amplitude, frequency, voltage, current, intensity, and/or waveform may be adjusted to achieve a desired result. Specifically, the degree in which the target site is stimulated to treat a specific medical condition can be controlled by adjusting these parameters. Preferably, the oscillating electrical signal is operated at a voltage between about 1 to about 60V. More preferably, the oscillating electrical signal is operated at a voltage between about 1 V to about 15 V. Preferably, the electric signal is operated at a frequency range between about 2 Hz to about 2500 Hz. More preferably, the electric signal is operated at a frequency range between about 2 Hz to about 200 Hz. Preferably, the pulse width of the oscillating electrical signal is between about 10 microseconds to about 1,000 microseconds. More preferably, the pulse width of the oscillating electrical signal is between about 50 microseconds to about 500 microseconds. The waveform may be, for example, biphasic square wave, sine wave, or other electrically safe and feasible combination. Preferably, the application of the oscillating electrical signal is: monopolar when the electrode is monopolar, bipolar when the electrode is bipolar, and multipolar when the electrode is multipolar. The electrode may be placed in permanent or temporary communication with the target site to provide chronic or acute stimulation to the target site. Specifically, the electrical neuromodulation can be temporary or short term, such as less than 10 days, intermediate (10-30 days) or chronic (greater than 30 days).

In embodiments where the therapy delivery device is a drug port and the therapy signal is a chemical signal, the chemical signal can be delivered instead of or in addition to the electrical signal delivered by an electrode according to the above-described embodiment. Specifically, a chemical agent may be delivered to a target site of the autonomic nervous system prior to, concurrent with, subsequent to or instead of the electrical neuromodulation. The chemical agent may be a neurotransmitter mimick; neuropeptide; hormone; pro-hormone; antagonist, agonist, reuptake inhibitor, or degrading enzyme thereof; peptide; protein; pharmaceutical agent; amino acid; nucleic acid; stem cell or any combination thereof and may be delivered by a slow release matrix or drug pump. The chemical agents may be delivered continuously or intermittently and the chemical neuromodulation can be temporary or short term, such as less than 10 days, intermediate (10-30 days) or chronic (greater than 30 days).

Notwithstanding whether chemical and/or electrical neuromodulation is employed in the methods of the present invention, a closed-loop feedback mechanism may be employed in conjunction with such neuromodulation. In such an embodiment, a therapy signal is applied to a target site of the autonomic nervous system in response to a detected bodily activity associated with the medical condition. In particular, this embodiment includes placing a therapy delivery device in a vessel adjacent the autonomic nervous system target site, detecting a bodily activity of the body associated with the medical condition, and activating the therapy delivery device to apply a therapy signal to the target site in response to the detected bodily activity. Such bodily activity to be detected is any characteristic or function of the body, and includes, for example, respiratory function, body temperature regulation, blood pressure, metabolic activity, cerebral blood flow, pH levels, vital signs, galvanic skin responses, perspiration, electrocardiogram, electroencephalogram, action potential conduction, chemical production, body movement, response to external stimulation, speech, balance, motor activity, ocular activity, and cognitive function.

In another embodiment of the present invention, the bodily activity of the body includes an electrical or chemical activity of the body and may be detected by sensors located on or within the body. For example, such activity may be detected by sensors located within or proximal to the target site, distal to the target site but within the nervous system, or by sensors located distal to the target site outside the nervous system. Examples of electrical activity detected by sensors located within or proximal to the target site include sensors that measure neuronal electrical activity, such as the electrical activity characteristic of the signaling stages of neurons (i.e. synaptic potentials, trigger actions, action potentials, and neurotransmitter release) at the target site and by afferent and efferent pathways and sources that project to and from or communicate with the target site. For example, the sensors can measure, at any signaling stage, neuronal activity of any of the diffuse connections of the autonomic nervous system. In particular, the sensors may detect the rate and pattern of the neuronal electrical activity to determine the electrical signal to be provided to the electrode.

Examples of chemical activity detected by sensors located within or proximal to the target site include sensors that measure neuronal activity, such as the modulation of neurotransmitters, hormones, pro-hormones, neuropeptides, peptides, proteins, electrolytes, or small molecules by the target site and modulation of these substances by afferent and efferent pathways and sources that project to and from the autonomic nervous system or communicate with the autonomic nervous system.

With respect to detecting electrical or chemical activity of the body by sensors located distal to the target site but still within the nervous system, such sensors could be placed in the brain, the spinal cord, cranial nerves, and/or spinal nerves. Sensors placed in the brain are preferably placed in a layer-wise manner in the direction of increasing proximity to the interhemispheric fibers. For example, a sensor could be placed on the scalp (i.e. electroencephalogram), in the subgaleal layer, on the skull, in the dura mater, in the sub dural layer and in the parenchyma (i.e. in the frontal lobe, occipital lobe, parietal lobe, temporal lobe) to achieve increasing specificity of electrical and chemical activity detection. The sensors could measure the same types of chemical and electrical activity as the sensors placed within or proximal to the target site as described above.

With respect to detecting electrical or chemical activity by sensors located distal to the target site outside the nervous system, such sensors may be placed in venous structures and various organs or tissues of other body systems, such as the endocrine system, muscular system, respiratory system, circulatory system, urinary system, integumentary system, and digestive system or such sensors may detect signals from these various body systems. All the above-mentioned sensing systems may be employed together or any combination of less than all sensors may be employed together.

After the sensor(s) detect the relevant bodily activity associated with the medical condition, the sensors generate a sensor signal. The sensor signal is processed by a sensor signal processor and provides a control signal to the stimulation controller, which is a signal generator or drug pump depending on whether electrical or chemical neuromodulation is desired. The stimulation controller, in turn, generates a response to the control signal by activating the therapy delivery device. The therapy delivery device then applies a therapy signal to the target site of the autonomic nervous system to treat the medical condition. In the case of electrical neuromodulation, the control signal may be an indication to initiate, terminate, increase, decrease or change the rate or pattern of a pulsing parameter of the electrical stimulation and the therapy signal can be the respective initiation, termination, increase, decrease or change in rate or pattern of the respective pulsing parameter. In the case of chemical neuromodulation, the control signal can be an indication to initiate, terminate, increase, decrease or change the rate or pattern of the amount or type of chemical agent administered, and the therapy signal can be the respective initiation, termination, increase, decrease or change in the rate or pattern of the amount or type of chemical agent administered. The processing of closed-loop feedback systems for electrical and chemical stimulation are described in more detail in respective U.S. Pat. Nos. 6,058,331 and 5,711,316, both of which are incorporated by reference herein.

Although the application of sensors to detect bodily activity are within the scope and spirit of the present invention, the present invention also contemplates the relevant bodily activity to be detected without sensors. In such case the neuromodulation parameters are adjusted manually in response to the clinical course of the medical condition or to reporting by the patient.

In another embodiment, the present invention provides a method of stabilizing and/or optimizing or augmenting bodily functions by inserting a therapy delivery device in a vessel of the body and advancing the therapy delivery device in the vessel to a point adjacent a target site of the autonomic nervous system and activating the therapy delivery device to apply a therapy signal (electrical and/or chemical signal) to the target site to stabilize and/or optimize the bodily function as well as to enhance, augment, normalize, regulate, control and/or improve the normal and abnormal functioning of the various body organs/structures/systems (for example heart, lung, gastrointestinal, genitourinary, vascular, and other systems) that are innervated by the autonomic nervous system. This method can be performed in the operating room, procedure room or imaging (MRI, CT, X-ray, fluoroscopy or optical imaged guided) suite. The procedures can be carried out peri-operative or post-operative to a surgical operation as well as in an intensive care unit and any other commonly utilized in-patient and out-patient capacities. Preferably, the surgical operation includes procedures that may require heart bypass equipment, procedures that may require a respiratory ventilator, or surgeries where intravenous medications are used during and after surgery to influence cardiac and/or pulmonary function. In an alternative embodiment, this method is performed in a non-surgical setting where intravenous medications are used for sedation, analgesia and to stabilize cardiac function, such as in the setting of myocardial infarction.

The present invention also provides a method for minimizing or resolving side effects and morbidity associated with other therapies used for various disorders including medications, surgery, chemotherapy, and radiation.

The foregoing description has been set forth merely to illustrate the invention and is not intended as being limiting. Each of the disclosed aspects and embodiments of the present invention may be considered individually or in combination with other aspects, embodiments, and variations of the invention. In addition, unless otherwise specified, none of the steps of the methods of the present invention are confined to any particular order of performance. Modifications of the disclosed embodiments incorporating the spirit and substance of the invention may occur to persons skilled in the art and such modifications are within the scope of the present invention. For example, although methods of treating specific medical conditions are described with respect to electrical and chemical neuromodulation, other modes of neuromodulation can be used such as light, magnetism, sound, pressure, and heat/cold. Furthermore, all references cited herein are incorporated by reference in their entirety.

We claim:

1. A method for treating an endocrinological condition in a subject, the method comprising the steps of:
    inserting a therapy delivery device, comprising an electrode, into a vein or artery of the subject;
    advancing the therapy delivery device in the artery or vein to a point adjacent a cervical ganglion of the sympathetic nervous system (SNS) that innervates a component of the endocrine system, such that, upon activation, the therapy delivery device delivers an electrical signal to the cervical ganglion of the SNS; and
    activating the electrode to deliver an electrical signal to the cervical ganglion of the SNS to treat the endocrinological condition.

2. The method of claim 1, wherein the therapy device is advanced in the artery or vein to the point adjacent to a cervical ganglion of the SNS, and wherein the cervical ganglion is at least one of a superior cervical ganglion, a middle cervical ganglion, an inferior cervical ganglion, and a cervicothoracic ganglion.

3. The method of claim 1, wherein the therapy delivery device is delivered into an artery of the subject, and wherein the artery is selected from a group consisting of inferior and superior thyroid arteries, carotid arteries, hypophyseal arteries, a celiac trunk, an aorta, iliac arteries, mesenteric arteries, and renal arteries.

4. The method of claim 1, wherein the therapy delivery device is delivered into a vein of the subject, and wherein the vein is selected from a group consisting of inferior and superior thyroid veins, jugular veins, hypophyseal veins, vena cavas, iliac veins, mesenteric veins, and renal veins.

5. The method of claim 1, further comprising:
    sensing a bodily activity associated with the endocrinological condition and generating a sensor signal; and
    adjusting the frequency within the frequency range of the electrical signal to the cervical ganglion of the SNS in response to the sensor signal to improve the endocrinological condition in the subject.

6. A method for treating an endocrinological condition in a subject, said method comprising the steps of:
    inserting an electrode into a vein or artery of the subject;
    advancing the electrode in the artery or vein to a point adjacent a cervical ganglion of the SNS that innervates a component of the endocrine system, such that, upon activation, the therapy delivery device delivers an electrical signal to the cervical ganglion of the SNS; and
    activating the electrode to deliver an electrical signal to the cervical ganglion of the SNS to treat the endocrinological condition, wherein the endocrinological condition is hypoglycemia, diabetes, hyperthyroidism, hypothyroidism, chronic fatigue syndrome, or Raynaud's syndrome.

7. The method of claim 6, wherein the cervical ganglion of the SNS is at least one of a superior cervical ganglion, a middle cervical ganglion, an inferior cervical ganglion, and a cervicothoracic ganglion.

8. The method of claim 6, wherein the electrode is implanted into the artery of the subject, and wherein the artery is selected from a group consisting of inferior and superior thyroid arteries, carotid arteries, hypophyseal arteries, a celiac trunk, an aorta, iliac arteries, mesenteric arteries, and renal arteries.

9. The method of claim 6, wherein the vein is selected from a group consisting of inferior and superior thyroid veins, jugular veins, hypophyseal veins, vena cavas, iliac veins, mesenteric veins, and renal veins.

10. The method of claim 6, further comprising:
    sensing a bodily activity associated with the endocrinological condition and generating a sensor signal; and
    adjusting the frequency within the frequency range of the electrical signal to the cervical ganglion of the SNS in response to the sensor signal to improve the endocrinological condition in the subject.

11. A method of treating an endocrinological condition in a subject, said method comprising the steps of:
    inserting a therapy delivery device into an artery or a vein of the subject;
    advancing the therapy delivery device in the artery or vein to a point adjacent a cervical ganglion of the sympathetic nervous system (SNS) that innervates a component of the endocrine system, such that, upon activation, the therapy delivery device delivers an electrical signal to the cervical ganglion of the SNS;
    activating the therapy delivery device to deliver an electrical signal to the cervical ganglion of the SNS;
    sensing a bodily activity associated with the endocrinological condition and generating a sensor signal; and
    activating the therapy delivery device to adjust the frequency of the electrical signal to the cervical ganglion of the SNS in response to the sensor signal to improve the endocrinological condition in the subject.

* * * * *